US005693310A

United States Patent [19]
Gries et al.

[11] Patent Number: 5,693,310
[45] Date of Patent: Dec. 2, 1997

[54] AMIDE COMPLEXES

[75] Inventors: Heinz Gries; Bernd Raduechel; Hans-Joachim Weinmann; Wolfgang Muetzel; Ulrich Speck, all of Berlin, Germany

[73] Assignee: Schering Aktiengesellschaft, Berlin, Germany

[21] Appl. No.: 614,947

[22] Filed: Nov. 19, 1990

Related U.S. Application Data

[63] Continuation of Ser. No. 494,803, Mar. 14, 1990, abandoned, which is a continuation of Ser. No. 100,681, Sep. 24, 1987, abandoned.

[30] Foreign Application Priority Data

Sep. 26, 1986 [DE] Germany .................. 36 33 245.3
Sep. 26, 1986 [DE] Germany .................. 36 33 246.1

[51] Int. Cl.$^6$ .................. C07F 5/00; C07C 229/00; A61K 49/00
[52] U.S. Cl. .................. 424/9.365; 546/300; 546/304; 546/314; 546/5; 546/242; 546/244; 546/246; 548/104; 548/182; 548/188; 548/194; 548/200; 548/225; 548/233; 548/235; 548/324.1; 548/326.5; 548/334.1; 548/369.4; 548/371.7; 548/374.1; 548/403; 548/540; 562/564; 562/565; 534/16; 544/64; 544/88; 544/97; 544/106; 544/162; 544/168; 544/190; 544/191; 544/198; 544/225; 544/298; 544/322; 544/355; 544/359; 544/382; 544/384; 544/399; 544/408; 544/410
[58] Field of Search .................. 424/9, 9.365; 436/173; 562/564, 565; 534/15, 16; 544/4.64, 88, 86, 111, 162, 121, 130, 133, 137, 139, 140, 141; 546/5; 548/104

[56] References Cited

U.S. PATENT DOCUMENTS

| | | | |
|---|---|---|---|
| 2,428,353 | 10/1947 | Bersworth .................. | 562/565 X |
| 2,524,218 | 10/1950 | Bersworth .................. | 562/564 X |
| 2,808,435 | 10/1957 | Young, Jr. . | |
| 2,811,550 | 10/1957 | Young, Jr. . | |
| 2,921,960 | 1/1960 | Kirtstahler et al. . | |
| 3,859,337 | 1/1975 | Herz et al. .................. | 544/162 X |
| 3,898,070 | 8/1975 | Dazzi . | |
| 4,352,751 | 10/1982 | Wieder et al. .................. | 424/1.1 X |
| 4,432,907 | 2/1984 | Wieder et al. . | |
| 4,647,447 | 3/1987 | Gries et al. . | |
| 4,687,659 | 8/1987 | Quay .................. | 534/16 X |
| 4,758,422 | 7/1988 | Quay .................. | 534/15 X |
| 4,826,673 | 5/1989 | Dean et al. .................. | 424/9 |
| 4,859,451 | 8/1989 | Quay et al. . | |
| 5,011,925 | 4/1991 | Rajagopalan .................. | 544/58.1 |
| 5,039,512 | 8/1991 | Kraft et al. .................. | 424/9 |
| 5,077,037 | 12/1991 | Wallace .................. | 424/9 |
| 5,087,439 | 2/1992 | Quay .................. | 424/9 |
| 5,087,440 | 2/1992 | Cacheris et al. .................. | 424/9 |
| 5,130,120 | 7/1992 | Weber .................. | 424/9 |
| 5,137,711 | 8/1992 | Weber et al. .................. | 424/9 |
| 5,217,706 | 6/1993 | Rajagopalan et al. .................. | 424/9 |
| 5,316,756 | 5/1994 | Gries et al. .................. | 424/9 |

FOREIGN PATENT DOCUMENTS

| | | | |
|---|---|---|---|
| 1253514 | 5/1989 | Canada . | |
| 3324235 | 1/1985 | Germany . | |
| 721640 | 1/1955 | United Kingdom .................. | 562/565 |
| 738306 | 10/1955 | United Kingdom .................. | 562/565 |

OTHER PUBLICATIONS

McGraw–Hill Dictionary of Scientific and Technical Terms, pp. 732 and 1054 1976.
"Intravascular Contrast Media–the Past, the Present and the Future", 1982, The British Journal of Radiology, vol. 55, No. 649:1–18.
Chem. Abstracts 92:24757c (Yamashita et al.) 1992.
Grant & Hackh's Chemical Dictionary, Fifth Edition, McGraw–Hill Book Co. p. 217, 1976.

*Primary Examiner*—John Kight
*Assistant Examiner*—Lara C. Kelley
*Attorney, Agent, or Firm*—Millen, White, Zelano & Branigan, P.C.

[57] ABSTRACT

Compounds of general Formula I $$Y-CH_2 \quad\quad CH_2CO-N\begin{smallmatrix}R^3\\R^4\end{smallmatrix} \quad (I)$$
$$\underset{XOOCCH_2R^1}{|}N-CH-(CH_2-N-CH_2)_n-CH-N\underset{CH_2COOX}{|}$$
$$\quad\quad\quad\quad CH_2COOX \quad R^2$$

wherein $R^3$ is a saturated, unsaturated, straight- or branched-chain or cyclic aliphatic hydrocarbon residue of up to 16 carbon atoms or, if $R^4$ is a hydrogen atom, a cycloalkyl group or an aryl or aralkyl group optionally substituted by one or several $C_1$–$C_6$-dialkylamino groups or by one or several $C_1$–$C_6$-alkoxy groups, $R^4$ is a hydrogen atom, a saturated, unsaturated, straight- or branched-chain or cyclic hydrocarbon residue of up to 16 carbon atoms, or $R^3$ and $R^4$ jointly mean a saturated or unsaturated 5- or 6-membered ring optionally substituted or containing an O, S, N atom or oxo substituent, and Y is COOX or $CONR_3R_4$.

are valuable complexing agents, complexes or complex salts, e.g., for use as NMR or X-ray diagnostic image-enhancement agents or radioactive diagnostic agents.

52 Claims, No Drawings

AMIDE COMPLEXES

This application is a continuation of application Ser. No. 07/494,803, filed Mar. 14, 1990 now abandoned, which is a continuation of Ser. No. 07/100,681, filed Sep. 24, 1987, now abandoned.

CROSS-REFERENCE TO RELATED APPLICATIONS

This application is related to U.S. applications Ser. No. 078,507 (Jul. 28, 1987), Ser. No. 063,355 (Jun. 18, 1987), Ser. No. 020,301 (Mar. 2, 1987), Ser. No. 020,300 (Mar. 2, 1987), Ser. No. 020,993 (Mar. 2, 1987), Ser. No. 020,992 (Mar. 2, 1987), Ser. No. 936,055 (Nov. 28, 1986), Ser. No. 876,497 (Jun. 20, 1986), and Ser. No. 627,143 (Jul. 2, 1984), each of which is a divisional, continuation or Continuation In Part of Ser. No. 573,184 (Jan. 23, 1984) (now U.S. Pat. No. 4,647,447) which is a Continuation In Part of 401,594 (Jul. 26, 1982), and is a Continuation In Part of all of said applications directly or indirectly, and all of which applications are entirely incorporated by reference herein.

BACKGROUND OF THE INVENTION

This invention relates to novel complexing agents, complexes, and complex salts, media containing these compounds and their use in diagnostics, as well as processes for producing these compounds and media, as well as to starting materials suitable therefor.

Metal complexes have been considered for contrast media in radiology as early as the beginning of the fifties. However, the compounds utilized at that time exhibited such a toxicity that use in human patients could not be contemplated. Therefore, it was very surprising to find that certain complex salts showed adequate compatibility so that routine use in man for diagnostic purposes could be considered.

Recently, complexes and complex salts have been introduced in Patent Applications EP 71564, EP 130934, DOS 3,401,052, PCT WO 86/02841, U.S. Pat. No. 4,687,659 and PCT WO 86/02005 as diagnostic agents, primarily for use in NMR diagnosis.

All of the heretofore known complexes and their salts cause problems in their clinical application with respect to compatibility and/or selectivity of binding and/or stability. Besides, the complexes disclosed in the two last-mentioned patent applications exhibit too high a lipophilic characteristic. These problems are the more pronounced, the higher the dosages that must be used for the products derived from the complexing agents. Thus far, actual beneficial utilization of heavy elements as components of X-ray contrast media to be administered parenterally has failed because of the inadequate compatibility of such compounds. In the paramagnetic substances heretofore proposed or tested for nuclear spin tomography, the gap between the effective dose and the dose that is toxic in animal experiments is relatively narrow and/or the substances exhibit a low organ specificity and/or stability and/or contrast enhancing effect and/or their compatibility is inadequate.

Consequently, there is a need for a variety of purposes for complex compounds which, above all, show improved compatibility, but also stability, good solubility, and adequate selectivity.

SUMMARY OF THE INVENTION

Accordingly, it is an object of this invention to provide such compounds and media, as well as to provide a process for their preparation and also suitable starting materials.

Upon further study of the specification and appended claims, further objects and advantages of this invention will become apparent to those skilled in the art.

It has been found that compounds having the anion of a complex-forming amide and one or several central ions of an element of atomic numbers 21–19, 31, 32, 38, 39, 42–44, 49, 57–83 and optionally one or several cations of an inorganic and/or organic base or amino acid surprisingly are excellently suitable for the production of NMR, X-ray and radio-diagnostica.

Thus, compounds of this invention include the physiologically compatible compounds of Formula I

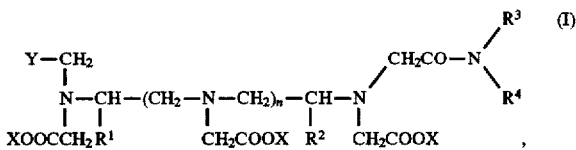

wherein n is a number 0, 1 or 2, $R^1$ and $R^2$ independently are hydrogen atoms, lower alkyl groups, phenyl groups, or benzyl groups or, when n is 0, jointly can also form a trimethylene or a tetramethylene group, $R^3$ is a saturated, unsaturated, straight- or branched-chain or cyclic aliphatic hydrocarbon residue of up to 16 carbon atoms and, when one $R^4$ is a hydrogen atom, at least one $R^3$ is a cycloalkyl group, or an aryl or aralkyl group optionally substituted by one or several $C_1$–$C_6$-dialkylamino groups or by one or several $C_1$–$C_6$-alkoxy groups, $R^4$ is a hydrogen atom, or a saturated, unsaturated, straight- or branched-chain or cyclic hydrocarbon residue of up to 16 carbon atoms, or $R^3$ and $R^4$ together form a saturated or unsaturated 5- or 6-membered ring, optionally substituted by one or several of $C_1$–$C_6$-alkyl, $C_1$–$C_5$-hydroxyalkyl, optionally hydroxylated or $C_1$–$C_6$-alkoxylated $C_2$–$C_6$-acyl, hydroxy, carbamoyl, carbamoyl-substituted $C_1$–$C_6$-alkyl, carbamoyl substituted at the carbamoyl nitrogen by one or two $C_1$–$C_6$-alkyl residue(s)—which can also form a ring optionally containing an oxygen atom—, or $C_1$–$C_6$-acylamino or $C_1$–$C_6$-alkylamino; this 5- or 6-membered ring optionally containing a further nitrogen, oxygen, or sulfur atom, or a carbonyl group, X is a hydrogen atom and/or a metal ion equivalent, Y is a COOX or

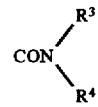

group, as well as their salts with organic and/or inorganic bases.

Compounds of Formula I wherein X is hydrogen are called complexing agents, and those wherein at least two of the substituents X are a metal ion equivalent are called metal complexes.

The element of the aforementioned atomic numbers forming the central ion of the physiologically compatible complex salt can, of course, also be radioactive for the desired purpose of using the diagnostic agent of this invention.

If the agent of this invention is intended for NMR diagnostics (see European Patent Application No. 71564), then the central ion of the complex salt will be paramagnetic. This is true, in particular, for the divalent and trivalent ions of the elements of atomic numbers 21–19, 42, 44 and 57–70. Suitable ions include, for example, the chromium(III), manganese(II), iron(II), cobalt(II), nickel(II), copper(II), praseodymium(III), neodymium(III), samarium(III) and ytterbium(III) ion. On account of their very strong magnetic moment, especially preferred are gadolinium(III), terbium (III), dysprosium(III), holmium(III), erbium(III) and iron (III) ions.

For utilization of the agents of this invention in nuclear-medicine diagnostics, the central ion must be radioactive. Suitable are, for example, radioisotopes of the elements copper, cobalt, gallium, germanium, yttrium, strontium, technetium, indium, ytterbium, gadolinium, samarium, and iridium. Further details are given in the documents cited above.

If the agent of this invention is intended for X-ray diagnostics and therapy, then the central ion will generally be derived from an element having a higher atomic number to attain adequate absorption of the X-rays. It has been found that diagnostic media are suitable for this purpose which contain a physiologically compatible complex salt with central ions of elements of atomic numbers of between 21–29, 42, 44, 57–83; these are, for example, the lanthanum (III) ion and the above-mentioned ions of the lanthanide series.

$R^1$ and $R^2$ as lower alkyl groups typically contain 1–8, preferably 1–4, C-atoms, e.g., methyl, ethyl, n- or i-propyl, n-, sec-, i-, or t-butyl, etc., including all isomers of pentyl, hexyl, heptyl and octyl.

Suitable aliphatic substituents $R^3$ and $R^4$ include saturated (e.g., alkyl), unsaturated (e.g., alkenyl), straight- or branched-chain or cyclic hydrocarbons of up to 16 carbon atoms, preferably 1–10 carbon atoms most preferably saturated hydrocarbons of 1–10 carbon atoms, especially saturated hydrocarbons of 1–5 carbon atoms. Examples include: methyl, ethyl, propyl, isopropyl, butyl, isobutyl, pentyl, cyclopentyl, cyclohexyl, propenyl, etc. Other suitable groups are the other alkyl groups mentioned for $R^1$ and $R^2$ and isomers containing 9–16 C-atoms as well as the alkenyl counterparts.

When $R^4$ is a hydrogen atom, at least one $R^3$ is $C_6$–$C_{10}$-aryl or $C_6$–$C_{10}$-Ar—$C_1$–$C_6$-alkyl, optionally substituted by one or several (e.g., up to three) di-$C_1$- to $C_6$-alkylamino groups or by one or several (e.g., up to three) $C_1$- to $C_6$-alkoxy groups, for example, a phenyl or benzyl group. When $R^4$ is H, said at least one $R^3$ can also be a cycloalkyl group as mentioned above preferably of 4–7 carbon atoms but generally of 3–16 carbon atoms.

The heterocyclic 5- or 6-membered ring formed by $R^3$ and $R^4$ with inclusion of the amide nitrogen can be saturated, unsaturated and/or substituted and can optionally contain a nitrogen, oxygen, sulfur atom or carbonyl group.

The heterocycle can be substituted by hydroxy, $C_1$–$C_6$-alkyl, for example methyl, ethyl, propyl, isopropyl, butyl, $C_1$–$C_5$-hydroxyalkyl, e.g. hydroxymethyl, hydroxyethyl, etc., $C_2$–$C_6$-acyl (e.g., alkanoyl), for example acetyl, propionyl, etc., which can optionally be substituted by hydroxy or $C_1$–$C_6$-alkoxy, e.g. methoxy, ethoxy, etc.

Carbamoyl is also a possible substituent, linked to the heterocycle directly or separated by a $C_1$–$C_6$-alkylene group, for example methylene, ethylene, propylene, etc. Carbamoyl can also be substituted at the nitrogen, if desired, by one or two $C_1$–$C_6$-alkyl residue(s), for example methyl, ethyl, propyl, isopropyl, etc., per above. The alkyl groups can optionally form a ring, e.g., with 5 or 6 members, such as, for example, a pyrrolidine or piperidine ring. The carbamoyl nitrogen can also be part of a morpholine ring, i.e., the latter ring can have an O atom. Another possible substituent of the heterocycle is an optionally $C_1$–$C_6$-alkylated or $C_1$–$C_6$-acylated (e.g., alkanoylated), primary or secondary amino group, such as, for example, the methyl-, ethyl-, acetyl-, propionyl-amino, etc., groups. If the heterocycle is substituted, the total number of substituents typically is 1 to 3.

Examples of suitable heterocycles include: pyrrolidinyl, piperidyl, pyrazolidinyl, pyrrolinyl, pyrazolinyl, piperazinyl, morpholinyl, imidazolidinyl, oxazolidinyl, thiazolidinyl, and the like.

If not all of the acidic hydrogen atoms are substituted by the central ion, then one, several, or all of the remaining hydrogen atom(s) can be replaced by cations of inorganic and/or organic bases or amino acids. Suitable inorganic cations include, for example, the lithium ion, the potassium ion, the calcium ion and, in particular, the sodium ion. Suitable cations of organic bases include, inter alia, those of primary, secondary or tertiary amines, e.g. ethanolamine, diethanolamine, morpholine, glucamine, N,N-dimethylglucamine and especially N-methylglucamine. Suitable cations of amino acids include, for example, those of lysine, of arginine, and of ornithine.

Introduction of amide groups for producing the complexing agents of this invention, i.e., compounds of general Formula I wherein X is hydrogen, takes place by conventional partial conversion of activated carboxy groups into amide groups of the respectively suited tetra-, penta- and hexacarboxylic acids—in correspondence with the desired final product. All synthesis possibilities known to one skilled in the art can be used for this process.

One example is the reaction of the anhydrides or esters of general Formulae II, IV, V and VI

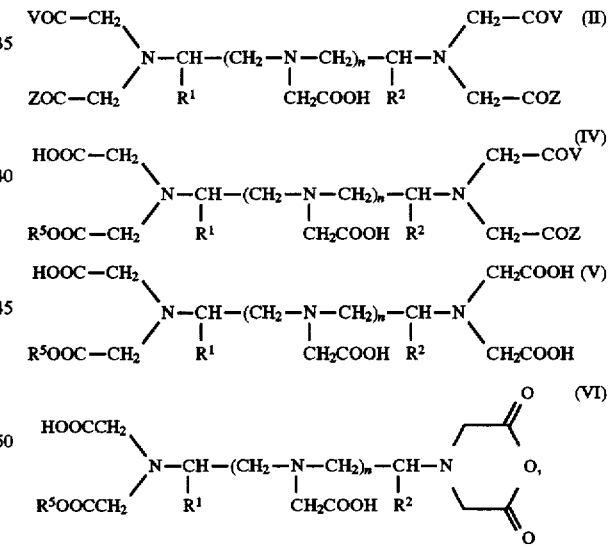

wherein $R^1$, $R^2$ and n have the meanings given above,

V and Z jointly mean an oxygen atom or

V is a hydroxy group and Z is the grouping $OR^5$, wherein $R^5$ is a $C_1$–$C_6$-alkyl residue, with amines of Formula III

wherein $R^3$ and $R^4$ have the meanings given above.

Examples of suitable amines include: dimethylamine, diethylamine, di-n-propylamine, diisopropylamine, di-n-butylamine, diisobutylamine, di-sec-butylamine, N-methyl-n-propylamine, dioctylamine, dicyclohexylamine, N-ethylcyclohexylamine, diisopropenylamine, benzylamine, aniline, 4-methoxyaniline, 4-dimethylaminoaniline, 3,5-dimethoxyaniline, morpholine, pyrrolidine, piperidine, N-methylpiperazine, N-ethylpiperazine, N-(2-hydroxyethyl)piperazine, N-(hydroxymethyl)piperazine, piperazinoacetic acid isopropylamide, N-(piperazinomethylcarbonyl)morpholine, N-(piperazinomethylcarbonyl)pyrrolidine 2-(2-hydroxymethyl)piperidine, 4-(2-hydroxyethyl)piperidine, 2-hydroxymethylpiperidine, 4-hydroxymethylpiperidine, 2-hydroxymethylpyrrolidine, 3-hydroxypiperidine, 4-hydroxypiperidine, 3-hydroxypyrrolidine, 4-piperidone, 3-pyrroline, piperidine-3-carboxylic acid amide, piperidine-4-carboxylic acid amide, piperidine-3-carboxylic acid diethylamide, piperidine-4-carboxylic acid dimethylamide, 2,6-dimethylpiperidine, 2,6-dimethylmorpholine, N-acetylpiperazine, N-(2-hydroxypropionyl)piperazine, N-(3-hydroxypropionyl)piperazine, N-(methoxyacetyl) piperazine, 4-(N-acetyl,N-methylamino)piperidine, piperidine-4-carboxylic acid (3-oxapentamethylene)amide, piperidine-3-carboxylic acid (3-oxapentamethylene)amide, N-(N',N'-dimethylcarbamoyl)piperazine, pyrazoline, pyrazolidine, imidazoline, oxazolidine, thiazolidine, etc.

Saponification of any ester groups that may still be present takes place according to methods known to those skilled in the art, for example, by means of alkaline hydrolysis.

The acid anhydrides of general Formula II can be prepared according to conventional methods, for example, by following the mode of operation described in U.S. Pat. No. 3,660,388 or in DOS 1,695,050 with acetic anhydride in pyridine. In certain cases, however, it is of special advantage to effect the step of splitting off water with carbodiimides gently in a suitable solvent, such as, for example, dimethylformamide or dimethylacetamide.

The production of the monoanhydrides of this invention according to general Formula VI shall be described, using as an example the monoanhydride of the ethyl ester of diethylenetriaminepentaacetic acid, starting with the monoethyl ester of DTPA (J. Pharm. Sci. 68:194, 1979):

$N^3$-(2,6-Dioxomorpholinoethyl)-$N^6$-(ethoxycarbonylmethyl)-3,6-diazaoctanedioic Acid A suspension of 21.1 g (50 mmol) of $N^3,N^6$-bis(carboxymethyl)-$N^9$-(ethoxycarbonylmethyl)-3,6,9-triazaundecanedioic acid in 250 ml of acetic anhydride is stirred, after adding 42.2 ml of pyridine, three days at room temperature. Then the precipitate is suctioned off, washed three times with respectively 50 ml of acetic anhydride, and then stirred for several hours together with absolute diethyl ether. After suctioning off, washing with absolute diethyl ether, and drying under vacuum at 40° C., 18.0 g (=89% of theory) of a white powder is obtained, mp 195°–196° C.

Analysis (based on anhydrous matter): C 47.64 H 6.25 N 10.42 (calculated) C 47.54 H 6.30 N 10.22 (found).

The reaction of the acid anhydrides to the amides of this invention can be carried out in the liquid phase. Suitable reaction media include, for example, water, dipolar aprotic solvents, such as acetonitrile, N-methyl-pyrrolidone, dimethylformamide, dimethylacetamide, and the like, or mixtures thereof. The reaction temperatures range between about 0° C. and 100° C., temperatures of 20°–80° C. being preferred. The reaction periods range between 0.5 hour and 2 days, preferably between 1 hour and 36 hours.

The esters of general Formula V are prepared conventionally, for example according to the methods described in R. A. Guilmette et al., J. Pharm. Sci. 68:194 (1979).

Aminolysis of the esters takes place in the liquid phase, for example in a suitable higher-boiling solvent, such as dimethylformamide, dimethylacetamide, or dimethyl sulfoxide. The reaction temperatures are about 20°–200° C., temperatures of 100°–180° C. being preferred. The reaction times range between 2 hours and 2 days, reaction times of between 4 hours and 36 hours being preferred.

Moreover, all methods known to one skilled in the art for converting carboxy groups into amide groups can be employed for the synthesis of the complexing agents according to Formula I of this invention, for example, the method according to Krejcarek and Tucker, Biochem. Biophys. Res. Commun. 77:581 (1977) by way of mixed anhydrides.

The thus-obtained compounds of Formula I wherein X is a hydrogen atom represent complex-forming agents. They can be isolated and purified, or they can be converted without isolation into metallic complexes of general Formula I wherein at least two of the substituents X mean a metal ion equivalent.

The preparation of the metal complexes of this invention takes place conventionally, e.g., in the way disclosed in Patents EP 71564, EP 130934, and DOS 3,401,052, by dissolving or suspending the metal oxide or a metal salt (e.g., the nitrate, acetate, carbonate, chloride or sulfate) of the element of atomic numbers 21–29, 31, 32, 38, 39, 42–44, 49, 57–83 in water and/or a lower alcohol (such as methanol, ethanol or isopropanol) and reacting with a solution or suspension of the equivalent amount of the complex-forming acid of Formula I wherein X is a hydrogen atom, and subsequently, if desired, substituting acidic hydrogen atoms of acid groups that are present by cations of inorganic and/or organic bases or amino acids.

In this procedure, neutralization is brought about with the aid of inorganic bases (e.g., hydroxides, carbonates or bicarbonates) of, for example, sodium, potassium or lithium and/or of organic bases, such as, inter alia, primary, secondary and tertiary amines, such as, for example, ethanolamine, morpholine, glucamine, N-methyl- and N,N-dimethylglucamine, as well as basic amino acids, such as, for example, lysine, arginine and ornithine.

For preparing the neutral complex compounds, such an amount of the desired bases can be added, for example, to the acidic complex salts in an aqueous solution or suspension that the neutral point is reached. The resultant solution can subsequently be concentrated to dryness under vacuum. It is frequently advantageous to precipitate the thus-formed neutral salts by adding water-miscible solvents, such as, for example, lower alcohols (methanol, ethanol, isopropanol, etc.), lower ketones (acetone, etc.), polar ethers (tetrahydrofuran, dioxane, 1,2-dimethoxyethane, etc.), and thus to obtain crystallized products that can be readily isolated and easily purified. It has proven to be especially advantageous to add the desired base as early as during the complex formation to the reaction mixture, thereby saving a process step.

If the acidic complex compounds contain several free acid groups, it is often advantageous to produce neutral mixed salts containing inorganic as well as organic cations as the counterions.

This can be done, for example, by reacting the complexing acid in an aqueous suspension or solution with the oxide or salt of the element yielding the central ion, and half the quantity of an organic base required for neutralization; isolating the thus-formed complex salt; optionally purifying same; and then combining same for complete neutralization with the required amount of inorganic base. The sequence of adding the bases can also be performed in the reverse order.

For complex compounds that contain radioisotopes, these can be prepared according to the methods disclosed in "Radiotracers for Medical Applications", volume I, CRC Press, Boca Raton, Fla.

The diagnostic media of this invention are likewise prepared conventionally by suspending or dissolving the complex compounds of this invention—optionally with addition of the additives customary in galenic pharmacy—in an aqueous medium and then optionally sterilizing the suspension or solution. Suitable additives are, for example, physiologically acceptable buffers (such as, for example, tromethamine), small additions of complexing agents (such as, for example, diethylenetriaminepentaacetic acid), or, if necessary, electrolytes, such as, for example, sodium chloride or, if necessary, antioxidants, such as, for example, ascorbic acid.

If suspensions or solutions of the agents of this invention in water or physiological saline solution are desirable for enteral administration or other purposes, then they can be mixed with one or several of the auxiliary agents customary in galenic pharmacy (for example, methylcellulose, lactose, mannitol) and/or tensides (for example, lecithins, "Tweens", "Myrj") and/or flavoring materials to improve taste (e.g., ethereal oils).

In principle, it is also possible to prepare the diagnostic media of this invention even without isolating the complex salts. In any event, special care must be directed toward effecting the chelate formation in such a way that the salts and salt solutions according to the invention are practically devoid of uncomplexed, toxically active metal ions. This can be ensured, for example, with the aid of dye indicators, such as xylenol orange, by control titrations during the manufacturing process. Therefore, the invention also relates to processes for the production of the complex compounds and their salts. Purification of the isolated complex salt remains as a final safety measure.

The diagnostic media according to this invention preferably contain 1 μmol-1 mol/l of the complex salt and are normally administered in doses of 0.001–5 mmol/kg. They are intended for enteral and parenteral administration, to mammals, including humans, e.g., analogously to Gd-DTPA.

The complex compounds of this invention are utilized:
(1) for NMR and X-ray diagnostics in the form of their complexes with the ions of the elements with atomic numbers 21–29, 42, 44 and 57–83; or
(2) for radiodiagnostics and radiotherapy in the form of their complexes with the radioisotopes of the elements with atomic numbers 27, 29, 31, 32, 38, 39, 43, 49, 64, 70 and 77.

The agents of this invention fulfill the variegated prerequisites for suitability as contrast media for nuclear spin tomography. Thus, they are excellently suited for improving the informative content of the image obtained with the aid of the nuclear spin tomograph upon oral or parenteral administration. The complex compounds according to the invention can also be utilized with advantage as shift reagents as well as for affecting the magnetic properties of atomic nuclei of other elements, such as, for example, $^{19}F$ and $^{31}P$. Furthermore, they show the high efficacy required for burdening the body with minimum amounts of foreign substances, and the good compatibility required for maintaining the noninvasive character of the examinations.

The good water solubility of the agents of this invention makes it possible to prepare highly concentrated solutions, thus maintaining the volume load on the circulation within tolerable limits and compensating for dilution by body fluids, i.e., NMR diagnostica must exhibit a water solubility that is 100 to 1,000 times higher than for purposes of in vitro NMR spectroscopy. Furthermore, the agents of this invention do not only exhibit high stability in vitro, but also a surprisingly high stability in vivo, so that a release or exchange of the ions—toxic per se—not bound in a covalent fashion in the complexes takes place only extremely gradually within the time period during which the novel contrast media are again completely eliminated.

In general, the agents of this invention are made into doses, as NMR diagnostic media, of amounts of 0.001–5 mmol/kg, preferably 0.005–0.5 mmol/kg. Details of use are discussed, for example, in H. J. Weinmann et al., Am. J. of Roentgenology 142:619 (1984). Especially low doses (below 1 mg/kg) of organ-specific NMR diagnostica are usable, for example, for the detection of tumors and of cardiac infarctions.

The agents of this invention are likewise suitable as radiodiagnostic media on account of their favorable radioactive properties and the good stability of the complex compounds contained therein. Details of their usage and dosage are disclosed, for example, in "Radiotracers for Medical Applications", CRC Press, Boca Raton, Fla.

The media of this invention are excellently suited as X-ray contrast agents; in this connection, it should be especially emphasized that their use does not bring about any indications of anaphylaxis-type reactions in biochemical-pharmacological tests, as known from the iodine-containing contrast media. They are particularly valuable, on account of their favorable absorption properties in regions of higher tube voltages, for digital subtraction techniques. In general, the agents of this invention, for use as X-ray contrast media, are made into doses and used in analogy to, for example, meglumine diatrizoate, amounting to 0.1–5 mmol/kg, preferably 0.25–1 mmol/kg.

Details of use of X-ray contrast media are discussed, for example, in Barke, "Röntgenkontrastmittel" (X-Ray Contrast Media), G. Thieme, Leipzig (1970) and P. Thurn, E. B ücheler, "Einführung in die Röntgendiagnostik" (Introduction to X-Ray Diagnostics), G. Thieme, Stuttgart, N.Y. (1977).

In summation, it has thus been successfully accomplished to synthesize novel complexing agents, metal complexes, and metal complex salts which open up new possibilities in diagnostic and therapeutic medicine. This development appears desirable, above all, in the context of evolving novel imaging methods in medical diagnostics.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, cited above and below are hereby incorporated by reference.

EXAMPLE 1

(a) $N^6$-Carboxymethyl-$N^3$-ethoxycarbonylmethyl-$N^9$-3-oxapentamethylenecarbamoylmethyl-3,6,9-triazaundecanedioic Acid A suspension is prepared from 2.42 g (6 millimoles) of $N^3$-(2,6-dioxomorpholinoethyl)-$N^6$-

(ethoxycarbonylmethyl)-3,6-diazaoctanedioic acid in 30 ml of dimethylformamide. Then, at −5° C., 3.04 g (30 mmol) of triethylamine and 0.52 ml (6 mmol) of morpholine are added; the mixture is stirred at this temperature for 2 hours, then overnight at room temperature. The solution is concentrated to dryness under vacuum and the residue stirred several hours with 100 ml of diisopropyl ether, suctioned off and, after recrystallization from ethanol, 2.2 g (76% of theory) of a white powder is obtained, mp 130° C. (with foaming).

Analysis (based on anhydrous matter): C 48.97 H 6.99 N 11.41 (calculated) C 48.78 H 7.15 N 11.55 (found)

(b) $N^3,N^6$-Bis(carboxymethyl)-$N^9$-3-oxapentamethylenecarbamoylmethyl-3,6,9-triazaundecanedioic Acid A solution is prepared of 0.74 g (1.5 mmol) of the compound obtained in (a) in 12 ml of water and 3 ml (15 mmol) of 5N sodium hydroxide solution. The solution is stirred for 2 hours at room temperature, brought to pH 7 by adding "Amberlite" IR 120, the filtrate is concentrated to 10 ml, acidified by adding 8 ml of "Amberlite" IR 120, suctioned off, and the filtrate is concentrated to dryness under vacuum, thus obtaining 720 mg (100% of theory) of a white powder which contains hydrate water, mp 122° C. (with foaming).

Analysis (based on anhydrous matter): C 46.75 H 6.54 N 12.11 (calculated) C 46.52 H 6.80 N 12.02 (found)

(c) Sodium Salt of the Gadolinium(III) Complex of $N^3,N^6$-Bis(carboxymethyl)-$N^9$-3-oxapentamethylenecarbamoylmethyl-3,6,9-triazaundecanedioic Acid 720 mg (1.5 mmol) of the compound obtained in (b) is heated in 5 ml of water at 50° C. with 371 mg (0.75 mmol) of gadolinium(III) carbonate, $Gd_2(CO_3)_3$, until no more carbon dioxide is released. Then the solution is brought to pH 7.2 by adding 0.1N sodium hydroxide solution, and the solution is concentrated to dryness under vacuum. After drying under vacuum at 50° C., 980 mg of a white powder, which contains hydrate water, is obtained having a decomposition point above 300° C.

Analysis (based on anhydrous matter): C 33.85 H 4.10 N 8.77 Gd 24.62 (calc.) C 33.71 H 4.41 N 8.50 Gd 24.30 (found)

EXAMPLE 2

(a) Gadolinium(III) Complex of $N^6$-Carboxymethyl-$N^3,N^9$-bis(3-oxapentamethylenecarbamoylmethyl)-3,6,9-triazaundecanedioic Acid 7.15 g (20 mmol) of 1,5-bis(2,6-dioxomorpholino)-3-azapentane-3-acetic acid is dissolved in a mixture of 5.23 ml (60 mmol) of morpholine and 55 ml of water. After 16 hours, the mixture is combined with 6.69 g (20 mmol) of gadolinium(III) acetate, dissolved in 80 ml of water; the mixture is stirred overnight and the reaction solution is passed over a column with 200 ml of anion exchanger IRA 410. Elution is performed with 1 liter of water, and the eluate is applied to 80 ml of cation exchanger IRC 50. Elution is carried out with water (1.5 liter), the eluate is concentrated under vacuum to 200 ml, and the solution is stirred for 30 minutes with 10 ml of anion exchanger IRA 410, suctioned off, and the filtrate is stirred for another 30 minutes with 10 ml of cation exchanger IRC 50, suctioned off, and evaporated under vacuum. The residue is pulverized and dried under vacuum at 70° C., thus obtaining 8.90 g of the title compound as a white powder, mp above 300° C.

Analysis (based on anhydrous matter): C 38.53 H 5.00 Gd 22.93 N 10.21 (calculated) C 38.31 H 5.07 Gd 23.19 N 10.08 (found)

(b) Gadolinium(III) complex of $N^6$-carboxymethyl-$N^3,N^9$-bis(tetramethylenecarbamoylmethyl)-3,6,9-triazaundecanedioic acid by reaction with pyrrolidine.

Properties: white powder having a melting point of above 300° C.

Analysis (based on anhydrous matter): C 40.42 H 5.24 Gd 24.05 N 10.71 (calculated) C 40.24 H 5.05 Gd 24.05 N 10.75 (found)

(c) Gadolinium(III) complex of $N^6$-carboxymethyl-$N^3,N^9$-bis(pentamethylenecarbamoylmethyl)-3,6,9-triazaundecanedioic acid by reaction with piperidine.

Properties: white powder having a melting point of above 300° C.

Analysis (based on anhydrous matter): C 42.28 H 5.62 Gd 23.06 N 10.27 (calculated) C 42.01 H 5.57 Gd 23.24 N 10.31 (found)

(d) Gadolinium(III) complex of $N^6$-carboxmethyl-$N^3,N^9$-bis[N,N-3-(2-hydroxyethyl)-3-azapentamethylenecarbamoylmethyl]-3,6,9-triazaundecanedioic acid by reaction with N-(2-hydroxyethyl)piperazine.

Properties: white powder having a melting point of above 300° C.

Analysis (based on anhydrous matter): C 40.46 H 5.75 Gd 20.37 N 12.70 (calculated) C 40.53 H 5.91 Gd 20.18 N 12.55 (found)

(e) Gadolinium(III) complex of $N^6$-carboxmethyl-$N^3,N^9$-bis[N,N-(1-hydroxymethyl)pentamethylenecarbamoylmethyl]-3,6,9-triazaundecanedioic acid by reaction with 2-hydroxymethylpiperidine.

Properties: white powder having a melting point of above 300° C.

Analysis (based on anhydrous matter): C 42.09 H 5.71 Gd 21.20 N 9.44 (calculated) C 42.01 H 5.62 Gd 21.45 N 9.53 (found)

EXAMPLE 3

Sodium Salt of the Gadolinium(III) Complex of $N^3,N^6$-bis(carboxymethyl)-$N^9$-3-oxapentamethylenecarbamoylmethyl-3,6,9-triazaundecanedioic Acid In a one-liter autoclave, 42.1 g (0.1 mol) of $N^3,N^6$-bis(carboxymethyl)-$N^9$-ethoxycarbonylmethyl-3,6,9-triazaundecanedioic acid (prepared according to J. Pharm. Sci. 68:194 [1979]) is heated with 87.12 g (1 mol) of morpholine for 30 hours to 110° C. After cooling, the mixture is dissolved in 200 ml of methanol and concentrated to dryness under vacuum. The residue is dissolved in 500 ml of water and combined with 41.2 g (0.1 mol) of gadolinium (III) acetate (water content 18.9%). The solution is stirred for 2 hours at room temperature, demineralized over "Amberlite" IRA 410, and then over "Amberlite" IR 120, and the filtrate is brought to pH 7.2 by adding 2N sodium hydroxide solution. After freeze-drying, 68.5 g (96.3% of theory) of the desired salt is obtained as the tetrahydrate in the form of a white powder, mp 275° C. (with foaming).

Analysis (based on anhydrous matter): C 33.85 H 4.10 N 8.77 Gd 24.62 (calculated) C 33.93 H 4.25 N 8.91 Gd 24.48 (found)

EXAMPLE 4

Mn(II) Complex of trans-1,2-Diamino-N,N'-bis(carboxymethyl)-N,N'-bis(3-oxapentamethylenecarbamoylmethyl)cyclohexane 9.3 g (30 mmol) of 4,4'-(trans-1,2-cyclohexanediyl)bis(2,6-morpholinedione), prepared according to DOS DE 3,324, 236, is suspended in 50 ml of water and combined with 5.23 ml (60 mmol) of morpholine. After 16 hours of agitation at room temperature, the clear reaction solution is combined with 3.45 g (30 mmol) of manganese(II) carbonate, $MnCO_3$, under gaseous nitrogen. After $CO_2$ evolution has ceased, the solution is freeze-dried, thus obtaining 18.4 g of the title compound as a brown powder which contains hydrate water and has a decomposition point above 300° C.

Analysis (based on anhydrous matter): C 49.16 H 6.38 N 10.42 Mn 10.22 (calculated) C 49.33 H 6.52 N 10.20 Mn 10.50 (found)

EXAMPLE 5

Gadolinium(III) Complex of 3,6,9-Tris(carboxymethyl)-3,6,9-triazaundecanedioic Acid N,N'-Bis(2-carbamoylpentamethylene)diamide Under agitation, a solution of 8.09 g (60 mmol; 95% strength) of piperidine-3-carboxylic acid amide in 80 ml of water is combined with 7.15 g (20 mmol) of 1,5-bis(2,6-dioxomorpholino)-3-azapentane-3-acetic acid; the mixture is stirred for 20 hours at room temperature and then combined with 6.69 g (20 mmol) of gadolinium(III) acetate dissolved in 80 ml of water. After another 24 hours, the reaction solution is passed over a column with 20 ml of anion exchanger IRA 410, eluted with 1 liter of water, and the eluate is poured on 80 ml of a cation exchanger IRC 50. The eluate is concentrated to about 200 ml under vacuum, the solution is stirred with 10 ml of IRA 410, filtered, agitated with 10 ml of IRC 50, filtered, and the solution evaporated under vacuum. Yield: 11.2 g of the title compound as a white powder, mp above 300°, water content: 3.45%.

Analysis (based on anhydrous matter): Calculated: C 40.67 H 5.25 Gd 20.48 N 12.77 Found: C 40.74 H 5.44 Gd 20.33 N 12.78

EXAMPLE 6

Gadolinium(III) Complex of 3,6,9-Tris(carboxymethyl)-3,6,9-triazaundecanedioic Acid N,N'-Bis(3-carbamoylpentamethylene)diamide Using, in place of the piperidine-3-carboxylic acid amide of Example 5, 60 mmol of piperidine-4-carboxylic acid amide, then 8.08 g of the gadolinium complex of 3,6,9-tris (carboxymethyl)-3,6,9-triazaundecanedioic acid N,N'-bis(3-carbamoylpentamethylene)diamide is obtained. Melting point above 300° C.; water content: 3.60%.

Analysis (based on anhydrous matter): Calculated: C 40.67 H 5.25 Gd 20.48 N 12.77 Found: C 40.62 H 5.80 Gd 20.39 N 12.59

EXAMPLE 7

N-Methylglucamine Salt of the Gadolinium(III) Complex of $N^3,N^6$-Bis(carboxymethyl)-$N^9$-diethylcarbamoylmethyl-3,6,9-triazaundecanedioic Acid In a 1-liter Autoclave, 42.1 g (0.1 mol) of $N^3,N^6$-bis (carboxymethyl)-$N^9$-ethoxycarbonylmethyl-3,6,9-triazaundecanedioic acid (produced according to J. Pharm. Sci. 68:194[1979]) is heated for 30 hours to 110° C. with 73.1 g (1 mol) of diethylamine. After cooling, 200 ml of methanol is dissolved and the mixture concentrated to dryness under vacuum, thus obtaining 73.4 g of the tetraethylammonium salt of $N^3,N^6$-bis(carboxymethyl)-$N^9$-diethylcarbamoylmethyl-3,6,9-triazaundecanedioic acid. The solution of the salt in 500 ml of water is combined with 41.2 g (0.1 mol) of gadolinium(III) acetate (water content 18.9%) and the mixture is stirred for 2 hours at room temperature. Then the solution is demineralized over ion exchangers and brought to pH 7.0 by adding N-methylglucamine. After freeze-drying, 74.3 g of the desired salt is obtained as a white powder which contains hydrate water and has a decomposition point lying above 300° C.

Analysis (based on anhydrous matter): C 37.68 H 5.69 N 8.79 Gd 19.73 (calculated) C 37.44 H 5.80 N 8.71 Gd 19.91 (found)

EXAMPLE 8

Gadolinium(III) Complex of $N^6$-Carboxymethyl-$N^3,N^9$-bis (dimethylcarbamoylmethyl)-3,6,9-triazaundecanedioic Acid In a 1-liter autoclave, 44.9 g (0.1 mol) of 6-carboxymethyl-3,9-bis(ethoxycarbonylmethyl)-3,6,9-triazaundecanedioic acid, prepared according to J. Pharm. Sci. 68:194 (1979), is heated with 100 ml of ethanol and 45 g (1 mol) of dimethylamine for 30 hours to 100° C. After cooling, the mixture is concentrated to dryness under vacuum and the residue dissolved in 200 ml of water. The mixture is combined with a solution of 41.20 g of gadolinium(III) acetate (0.1 mol, water content 18.87%) and stirred at room temperature for 2 hours. Then the solution is demineralized over ion exchangers and freeze-dried, thus obtaining 58.0 g (94% of theory) of the gadolinium(III) complex of $N^6$-carboxymethyl-$N^3,N^9$-bis (dimethylcarbamoylmethyl)-3,6,9-triazaundecanedioic acid as the monohydrate with a decomposition point lying above 305° C.

Analysis (based on anhydrous matter): C 35.93 H 5.03 N 11.64 Gd 26.13 (calculated) C 36.15 H 5.21 N 11.77 Gd 26.02 (found)

EXAMPLE 9

Sodium Salt of the Dysprosium(III) Complex of $N^3,N^6$-Bis (carboxymethyl)-$N^9$-phenylcarbamoylmethyl-3,6,9-triazaundecanedioic Acid (a) $N^3,N^6$-Bis(carboxymethyl)-$N^9$-phenylcarbamoylmethyl-3,6,9-triazaundecanedioic Acid In a 1-liter autoclave, 42.1 g (0.1 mol) of $N^3,N^6$-bis (carboxymethyl)-$N^9$-ethoxycarbonylmethyl-3,6,9-triazaundecanedioic acid is heated with 93.1 g (1 mol) of aniline for 30 hours to 110° C. After cooling, the content is dissolved in 800 ml of methanol and the solution concentrated to dryness under vacuum. The residue is combined with 800 ml of water and the excess aniline exhaustively extracted with methylene chloride. The aqueous phase is passed, after an initial distillation, over 100 ml of "Amberlite" IR 120. The acidic eluate is concentrated and the residue dried under vacuum at 50° C., thus obtaining 35.1 g (75% of theory) in the form of a white powder with a melting point of 125° C.

Analysis (based on anhydrous matter): C 51.27 H 6.03 N 11.96 (calculated) C 51.44 H 6.21 N 12.03 (found)

(b) 3.9 g (8.3 mmol) of the compound obtained in (a) is suspended in 50 ml of water and combined with 2.82 g (8.3 mmol) of dysprosium(III) acetate. The mixture is agitated for 2 hours at 60° C. and, after cooling to room temperature, the acetate ions are removed by way of an exchanger. The solution is brought to pH 7 by adding 0.1N sodium hydroxide solution. After concentration to dryness, the desired complex salt is obtained in a qualitative yield in the form of a yellowish powder containing hydrate water.

Analysis (based on anhydrous matter): C 36.96 H 3.72 N 8.62 Dy 25.00 (calculated) C 36.85 H 3.92 N 8.81 Dy 25.23 (found)

EXAMPLE 10

Gadolinium(III) Complex of $N^6$-Carboxymethyl-$N^3$,$N^9$-bis(N-methyl-N-n-propylcarbamoylmethyl)-3,6,9-triazaundecanedioic Acid 7.15 g (20 mmol) of 1,5-bis(2,6-dioxomorpholino)-3-azapentane-3-acetic acid is dissolved in a mixture of 4.39 g (60 mmol) of N-methyl-n-propylamine and 60 ml of water. After 20 hours, the solution is combined with 6.69 g (20 mmol) of gadolinium(III) acetate dissolved in 80 ml of water. After another 16 hours, the solution is filtered and the filtrate is allowed to pass through a column with 200 ml of anion exchanger IRA 410. The mixture is eluted with 1 liter of water and the eluate passed onto 80 ml of cation exchanger IRC 50. The eluate is then concentrated under vacuum to 150 ml, and the solution is stirred for one hour with 10 ml of anion exchanger IRA 410 and filtered. The filtrate is stirred for another hour with 10 ml of cation exchanger IRC 50, filtered, and the solution evaporated under vacuum. The residue is pulverized and dried under vacuum at 70° C., thus obtaining 8.73 g of the title compound as a white powder, mp above 300° C.

Analysis (based on anhydrous matter): C 40.17 H 5.82 Gd 23.90 N 10.65 (calculated) C 39.98 H 5.99 Gd 24.20 N 10.66 (found)

Proceeding in accordance with the above directions and replacing N-methyl-n-propylamine in each case by another amine, the following complex compounds are produced:

(a) Gadolinium(III) complex of $N^6$-carboxmethyl-$N^3$,$N^9$-bis(diethylcarbamoylmethyl)-3,6,9-triazaundecanedioic acid by reaction with diethylamine.

Properties: white powder having a melting point of above 300° C.

Analysis (based on anhydrous matter): C 40.17 H 5.82 Gd 23.90 N 10.65 (calculated) C 40.06 H 6.03 Gd 24.30 N 10.51 (found)

(b) Gadolinium(III) complex of $N^6$-carboxymethyl-$N^3$,$N^9$-bis(dimethylcarbamoylmethyl)-3,6,9-triazaundecanedioic acid by reaction with dimethylamine.

Properties: white powder having a melting point of above 300° C.

Analysis (based on anhydrous matter): C 35.93 H 5.03 Gd 26.13 N 11.64 (calculated) C 35.69 H 4.97 Gd 26.25 N 11.51 (found)

EXAMPLE 11

Mn(II) Complex of trans-1,2-Diamino-N,N'-bis(carboxymethyl)-N,N'-bis(dimethylcarbamoylmethyl)cyclohexane 9.3 g (30 mmol) of 4,4'-(trans-1,2-cyclohexanediyl)-bis(2,6-morpholinedione), prepared according to DOS DE 3,324,236, is suspended in 50 ml of water and combined with 4.5 g (100 mmol) of dimethylamine (aqueous solution). The mixture is stirred for 16 hours at room temperature and the solution is concentrated to dryness under vacuum. The residue of the dimethylammonium salt is dissolved in 100 ml of water and combined, under exposure to nitrogen gas, with 3.45 g (30 mmol) of manganese(II) carbonate, $MnCO_3$. After the release of $CO_2$ has ceased, the solution is freeze-dried, thus obtaining 15.2 g of the title compound as a brown powder which contains hydrate water and has a decomposition point lying above 300° C.

Analysis (based on anhydrous matter): C 47.68 H 6.67 N 12.36 Mn 12.12 (calculated) C 47.80 H 6.83 N 12.39 Mn 12.31 (found)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

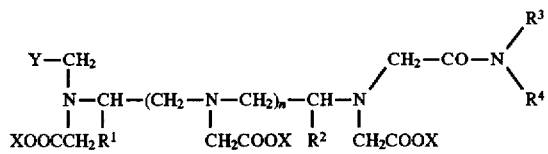

wherein n is 0, 1 or 2, $R^1$ and $R^2$ independently are hydrogen, $C_{1-8}$-alkyl, phenyl, or benzyl, and, when n is 0, $R^1$ and $R^2$ jointly form trimethylene or tetramethylene, $R^3$ is an aliphatic hydrocarbon group of up to 16 carbon atoms, and when $R^4$ is hydrogen, $R^3$ is a cyclic such group or $C_{6-10}$-aryl or $C_{6-10}$-ar-$C_{1-6}$-alkyl, or $C_{6-10}$-aryl or $C_{6-10}$-ar-$C_{1-6}$-alkyl substituted by di-$C_1$-$C_6$-alkylamino or by $C_1$-$C_6$-alkoxy, $R^4$ is hydrogen or an aliphatic hydrocarbon group of up to 16 carbon atoms, or $R^3$ and $R^4$ together form a saturated or unsaturated 5- or 6-membered ring, optionally containing an O, S or additional N atom, or optionally substituted by oxo, $C_1$-$C_6$-alkyl, $C_1$-$C_5$-hydroxyalkyl, $C_{2-6}$-alkanoyl, $C_{2-6}$-alkanoyl substituted by OH, $C_{2-6}$-alkanoyl substituted by $C_{1-6}$-alkoxy, hydroxy, carbamoyl, $C_1$-$C_6$-alkyl substituted by carbamoyl, carbamoyl substituted at the carbamoyl nitrogen by one or two $C_1$-$C_6$-alkyl group(s)—the latter optionally together forming a ring optionally containing an oxygen atom—, $C_1$-$C_6$-alkanoylamino, or $C_1$-$C_6$-alkylamino, X is hydrogen, a chelated metal ion equivalent, or a combination thereof, Y is COOX or

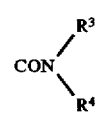

or a physiologically acceptable salt thereof at one or more X groups which are H, in each case independently with an organic base, inorganic base, or amino acid.

2. A compound of claim 1, wherein all X groups are hydrogen atoms.

3. A compound of claim 1, wherein at least two of the substituents X are chelated metal ion equivalents of at least one element of atomic numbers 21-29, 42, 44 or 57-83.

4. A compound of claim 1, wherein at least two of the substituents X are chelated metal ion equivalents of a radionuclide of at least one element of atomic numbers 27, 29, 31, 32, 38, 39, 43, 49, 62, 64, 70 or 77.

5. A compound of claim 1, wherein Y is COOX.

6. A compound of claim 1, wherein Y is

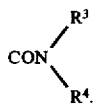

7. A compound of claim 1 which is a salt wherein the cation is from an organic or inorganic base or a combination thereof.

8. A compound of claim 1 wherein n is 1.

9. A compound of claim 1 wherein $R^1$ and $R^2$ are H.

10. A compound of the formula

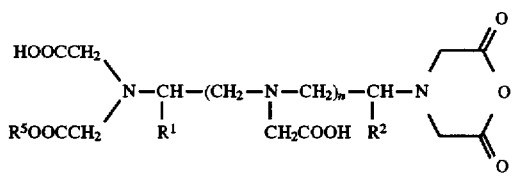

wherein n is 0 or 1, $R^1$ and $R^2$ each independently are hydrogen, $C_{1-8}$-alkyl, phenyl or benzyl, or, when n is 0, $R^1$ and $R^2$ can also jointly form trimethylene or tetramethylene, and $R^5$ is $C_1$-$C_6$-alkyl.

11. $N^3$-(2,6-Dioxomorpholinoethyl-$N^6$-(ethoxycarbonylmethyl)-3,6-diazaoctanedioic acid, a compound of claim 10.

12. $N^6$-Carboxymethyl-$N^3$-ethoxycarbonylmethyl-$N^9$-3-oxapentamethylenecarbamoylmethyl-3,6,9-triazaundecanedioic acid, $N^3,N^6$-bis(carboxymethyl)-$N^9$-3-oxapentamethylenecarbamoylmethyl-3,6,9-triazaundecanedioic acid, sodium salt of the gadolinium(III) complex of $N^3,N^6$-bis(carboxymethyl)-$N^9$-3-oxapentamethylenecarbamoylmethyl-3,6,9-triazaundecanedioic acid, gadolinium(III) complex of $N^6$-carboxymethyl-$N^3,N^9$-bis(3-oxapentamethylenecarbamoylmethyl)-3,6,9-triazaundecanedioic acid, gadolinium(III) complex of $N^6$-carboxymethyl-$N^3,N^9$-bis(tetramethylenecarbamoylmethyl)-3,6,9-triazaundecanedioic acid, gadolinium(III) complex of $N^6$-carboxymethyl-$N^3,N^9$-bis(pentamethylenecarbamoylmethyl)-3,6,9-triazaundecanedioic acid, gadolinium(III) complex of $N^6$-carboxymethyl-$N^3,N^9$-bis[N,N-3-(2-hydroxyethyl)-3-azapentamethylenecarbamoylmethyl]-3,6,9-triazaundecanedioic acid, gadolinium(III) complex of $N^6$-carboxymethyl-$N^3,N^9$-bis[N,N-(1-hydroxymethyl)pentamethylenecarbamoylmethyl]-3,6,9-triazaundecanedioic acid, sodium salt of the gadolinium(III) complex of $N^3,N^6$-bis(carboxymethyl)-$N^9$-(3-oxapentamethylene)carbamoylmethyl-3,6,9-triazaundecanedioic acid, manganese(II) complex of trans-1,2-diamino-N,N,-bis(carboxymethyl)-N,N'-bis(3-oxapentamethylenecarbamoylmethyl)cyclohexane, gadolinium(III) complex of 3,6,9-tris(carboxymethyl)-3,6,9-triazaundecanedioic acid N,N'-bis(2-carbamoylpentamethylene)diamide, gadolinium(III) complex of 3,6,9-tris(carboxymethyl)-3,6,9-triazaundecanedioic acid N,N'-bis(3-carbamoylpentamethylene)diamide, each a compound of claim 1.

13. A compound according to claim 1, wherein n is 1 or 2, $R^1$ and $R^2$ independently are hydrogen, $C_{1-8}$-alkyl, phenyl, or benzyl, $R^3$ and $R^4$ together form a saturated or unsaturated 5- or 6-membered ring, optionally containing an O, S or additional N atom, or optionally substituted by oxo, $C_{1-6}$-alkyl, $C_{1-5}$-hydroxyalkyl, $C_{2-6}$-alkanoyl, $C_{2-6}$-alkanoyl substituted by OH, $C_{2-6}$-alkanoyl substituted by $C_{1-6}$-alkoxy, hydroxy, carbamoyl, $C_{1-6}$-alkyl substituted by carbamoyl, carbamoyl substituted at the carbamoyl nitrogen by one or two $C_{1-6}$-alkyl group(s)— the latter optionally together forming a ring optionally containing an oxygen atom—, $C_{1-6}$-alkanoylamino, or $C_{1-6}$-alkylamine, X is hydrogen, a chelated metal ion equivalent, or a combination thereof, Y is COOX or

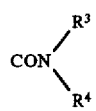

or a physiologically acceptable salt thereof at one or more X groups which are H, in each case independently with an organic base, inorganic base, or amino acid.

14. A compound of claim 13, wherein $R^3$ and $R^4$ together form pyrrolidinyl, piperidinyl or piperazinyl.

15. A compound of claim 13, wherein $R^3$ and $R^4$ together form morpholino.

16. A compound of claim 15, wherein Y is $CONR_3R_4$, n=1, and $R^1$ and $R^2$ are each H.

17. A compound of claim 16, wherein at least two X's are a chelated metal ion equivalent.

18. A compound according to claim 13, wherein said compound is a gadolinium(III) complex of $N^6$-carboxymethyl-$N^3,N^9$-bis(3-oxapentamethylenecarbamoylmethyl)-3,6,9-triazaundecanedioic acid.

19. A composition comprising a compound of claim 18 and a pharmaceutically acceptable carrier.

20. A compound according to claim 13, wherein $R^3$ and $R^4$ together form pyrrolidinyl, piperidyl, pyrazolidinyl, pyrrolinyl, pyrazolinyl, piperazinyl, morpholinyl, imidazolidinyl or thiazolidinyl.

21. A compound according to claim 1, wherein n is 0 and $R^1$ and $R^2$ jointly form trimethylene or tetramethylene.

22. A compound of claim 1, wherein three X groups represent a central gadolinium ion.

23. A compound of claim 1, wherein at least one X group which is H is replaced by lithium ion, potassium ion, calcium ion or sodium ion.

24. A compound of claim 1, wherein said amino acid is lysine, arginine or orthinine and said organic base is ethanolamine, diethanolamine, morpholine, glucamine, N,N-dimethylglucamine or N-methylglucamine.

25. A compound of the formula

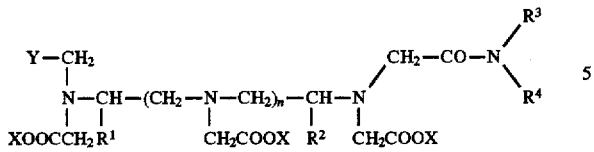

wherein n is 0, 1 or 2, $R^1$ and $R^2$ independently are hydrogen, $C_{1-8}$-alkyl, phenyl, or benzyl, and, when n is 0, $R^1$ and $R^2$ jointly form trimethylene or tetramethylene, $R^3$ is a cyclic aliphatic hydrocarbon group of up to 16 carbon atoms, $C_{6-10}$-aryl, $C_{6-10}$-ar-$C_{1-6}$-alkyl, $C_{6-10}$-aryl substituted by di-$C_1$-$C_6$-alkylamino or by $C_1$-$C_6$-alkoxy, or $C_{6-10}$-ar-$C_{1-6}$-alkyl substituted by di-$C_1$-$C_6$-alkylamino or by $C_1$-$C_6$-alkoxy, $R^4$ is hydrogen, X is in each case hydrogen or a chelated metal ion equivalent, Y is COOX or

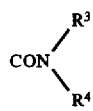

or a physiologically acceptable salt thereof at one or more X groups which are H, in each case independently with an organic base, inorganic base, or amino acid.

26. A compound according to claim 25, wherein said compound is a sodium salt of the dysprosium(III) complex of $N^3,N^6$-bis(carboxymethyl)-$N^9$-phenylcarbamoylmethyl-3,6,9-triazaundecanedioic acid.

27. A compound of the formula

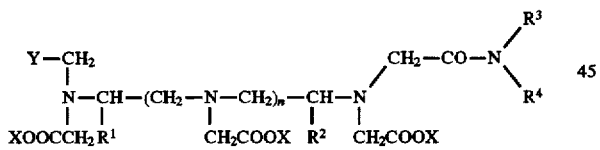

wherein n is 0, 1 or 2;

$R^1$ and $R^2$ independently are hydrogen, $C_{1-8}$-alkyl, phenyl, or benzyl, and, when n is 0, $R^1$ and $R^2$ jointly form trimethylene or tetramethylene;

$R^3$ is a cyclic aliphatic hydrocarbon group of up to 16 carbon atoms, and, if at least one $R^4$ is hydrogen, then $R^3$ can also be $C_{6-10}$-aryl, $C_{6-10}$-ar-$C_{1-6}$-alkyl, $C_{6-10}$-aryl substituted by di-$C_1$-$C_6$-alkylamino or by $C_1$-$C_6$-alkoxy, or $C_{6-10}$-ar-$C_{1-6}$-alkyl substituted by di-$C_1$-$C_6$-alkylamino or by $C_1$-$C_6$-alkoxy;

$R^4$ is hydrogen or a saturated or unsaturated, straight-chain, branched-chain, or cyclic hydrocarbon residue of up to 16 carbon atoms;

X is in each case hydrogen or a chelated metal ion equivalent;

Y is COOX or

or a physiologically acceptable salt thereof at one or more X groups which are H, in each case independently with an organic base, inorganic base, or amino acid.

28. A compound of the formula

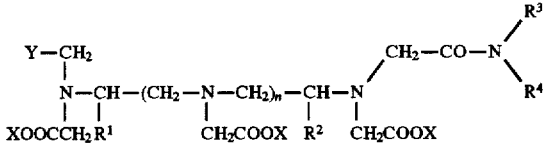

wherein n is 0;

$R^1$ and $R^2$ together form trimethylene or tetramethylene;

$R^3$ is an aliphatic hydrocarbon group of up to 16 carbon atoms;

$R^4$ is an aliphatic hydrocarbon group of up to 16 carbon atoms;

X is in each case hydrogen or a chelated metal ion equivalent;

Y is COOX or

or a physiologically acceptable salt thereof at one or more X groups which are H, in each case independently with an organic base, inorganic base, or amino acid.

29. A compound according to claim 28, wherein said compound is Mn(II) complex of trans-1,2-diamino-N,N'-bis(carboxymethyl)-N,N'-bis(dimethylcarbamoylmethyl)cyclohexane.

30. A compound of the formula

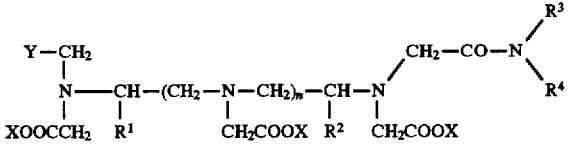

wherein n is 0, 1 or 2, $R^1$ is $C_{1-8}$-alkyl, phenyl, benzyl or, when n is 0, $R^1$ forms trimethylene or tetramethylene with $R^2$;

$R^2$ is hydrogen, $C_{1-8}$-alkyl, phenyl, benzyl, or when n is 0, $R^2$ forms trimethylene or tetramethylene with $R^1$;

$R^3$ is a saturated, unsaturated, straight- or branched-chain or cyclic aliphatic hydrocarbon residue of up to 16 carbon atoms and, when $R^4$ is a hydrogen atom, at least one $R^3$ is a cycloalkyl group or an aryl or aralkyl group optionally substituted by one or several $C_1$-$C_6$-dialkylamino groups or by one or several $C_1$-$C_6$-alkoxy groups;

$R^4$ is a hydrogen atom, or a saturated, unsaturated, straight- or branched-chain or cyclic hydrocarbon residue of up to 16 carbon atoms;

19

X is, in each case, hydrogen or a chelated metal ion equivalent;

Y is COOX or

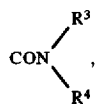

or a physiologically acceptable salt thereof, at one or more X groups which are H, in each case independently, with an organic base, inorganic base, or amino acid.

31. A compound of the formula

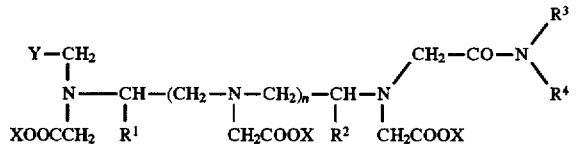

wherein n is 0, 1 or 2, $R^1$ is hydrogen, $C_{1-8}$-alkyl, phenyl, benzyl, or when n is 0, $R^1$ forms trimethylene or tetramethylene with $R^2$;

$R^2$ is $C_{1-8}$-alkyl, phenyl, benzyl or, when n is 0, $R^2$ forms trimethylene or tetramethylene with $R^1$;

$R^3$ is a saturated, unsaturated, straight- or branched-chain or cyclic aliphatic hydrocarbon residue of up to 16 carbon atoms and, when $R^4$ is a hydrogen atom, at least one $R^3$ is a cycloalkyl group or an aryl or aralkyl group optionally substituted by one or several $C_1$–$C_6$-dialkylamino groups or by one or several $C_1$–$C_6$-alkoxy groups;

$R^4$ is a hydrogen atom, or a saturated, unsaturated, straight- or branched-chain or cyclic hydrocarbon residue of up to 16 carbon atoms;

X is, in each case, hydrogen or a chelated metal ion equivalent;

Y is COOX or

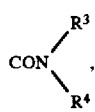

or a physiologically acceptable salt thereof, at one or more X groups which are H, in each case independently, with an organic base, inorganic base, or amino acid.

32. A compound according to claim 30, wherein n is 1 or 2 and $R^1$ is $C_{2-8}$-alkyl, phenyl or benzyl.

33. A compound according to claim 31, wherein n is 1 or 2 and $R^2$ is $C_{2-8}$-alkyl, phenyl or benzyl.

34. A compound according to claim 13, wherein $R^3$ and $R^4$ together form pyrrolidinyl, piperidyl, pyrazolidinyl, pyrrolinyl, pyrazolinyl, piperazinyl, morpholinyl, imidazolidinyl or thiazolidinyl.

35. A compound according to claim 1, wherein $R^3$ and $R^4$ together are not oxazolidinyl.

20

36. A compound of the formula

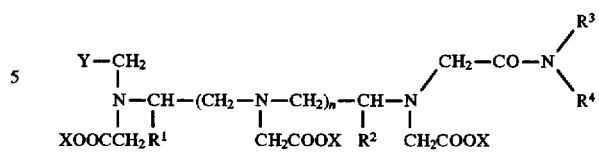

wherein n is 0, 1 or 2, $R^1$ and $R^2$ independently are hydrogen, $C_{1-8}$-alkyl, phenyl or benzyl, and, when n is 0, $R^1$ and $R^2$ jointly form trimethylene or tetramethylene;

$R^3$ and $R^4$ together form oxazolidinyl;

X is hydrogen, a chelated metal ion equivalent, or a combination thereof,

Y is COOX or

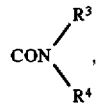

or a physiologically acceptable salt thereof, at one or more X groups which are H, in each case independently, with an organic base, inorganic base, or amino acid.

37. A pharmaceutical composition comprising at least one physiologically compatible compound of claim 1 and a pharmaceutically acceptable adjuvant.

38. A composition of claim 37 wherein the amount of said compound is 1 µmol to 1 mole per liter of composition.

39. A pharmaceutical composition according to claim 37, wherein said composition is sterile.

40. A pharmaceutical composition comprising at least one physiologically compatible compound of claim 3 and a pharmaceutically acceptable adjuvant.

41. A pharmaceutical composition according to claim 40, wherein said at least one element has an atomic number of 21–29, 42, 44 or 58–70.

42. A composition according to claim 37, further comprising a complexing agent.

43. A composition according to claim 40, further comprising a complexing agent.

44. A composition according to claim 41, further comprising a complexing agent.

45. A composition according to claim 37, which is physiologically suitable for enteral or parenteral administration.

46. A composition according to claim 40, which is physiologically suitable for enteral or parenteral administration.

47. A composition according to claim 41, which is physiologically suitable for enteral or parenteral administration.

48. A composition according to claim 37, which is physiologically suitable for administration to humans.

49. A composition according to claim 40, which is physiologically suitable for administration to humans.

50. A composition according to claim 41, which is physiologically suitable for administration to humans.

51. A composition according to claim 40, wherein said composition is sterile.

52. A composition according to claim 41, wherein said composition is sterile.

* * * * *

UNITED STATES PATENT AND TRADEMARK OFFICE
CERTIFICATE OF CORRECTION

PATENT NO. : 5,693,310

DATED : December 2, 1997

INVENTOR(S): Heinz GRIES et al.

It is certified that an error appears in the above-identified patent and that said Letters Patent is hereby corrected as shown below:

Column 14, lines 25 through 31, please delete in their entirety.

Signed and Sealed this

Twenty-sixth Day of December, 2000

Attest:

Q. TODD DICKINSON

*Attesting Officer*  *Director of Patents and Trademarks*